United States Patent
Dong

(10) Patent No.: US 10,481,063 B2
(45) Date of Patent: Nov. 19, 2019

(54) DISPLAY DEVICE

(71) Applicant: BOE Technology Group Co., Ltd., Beijing (CN)

(72) Inventor: Wenchu Dong, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 275 days.

(21) Appl. No.: 15/512,171

(22) PCT Filed: Apr. 14, 2016

(86) PCT No.: PCT/CN2016/079252
§ 371 (c)(1),
(2) Date: Mar. 17, 2017

(87) PCT Pub. No.: WO2016/177263
PCT Pub. Date: Nov. 10, 2016

(65) Prior Publication Data
US 2017/0276587 A1  Sep. 28, 2017

(30) Foreign Application Priority Data
May 6, 2015  (CN) .......................... 2015 1 0227976

(51) Int. Cl.
H04N 7/18   (2006.01)
G01N 15/06  (2006.01)
(Continued)

(52) U.S. Cl.
CPC ........... *G01N 15/06* (2013.01); *B01D 50/004* (2013.01); *G01N 15/1427* (2013.01);
(Continued)

(58) Field of Classification Search
CPC .. B01D 50/004; G01N 15/06; G01N 15/1427; G06K 9/00624; G06K 9/00785; G08B 21/12
(Continued)

(56) References Cited

U.S. PATENT DOCUMENTS 4,499,377 A * 2/1985 Presser .............. G01N 33/0006
                                                    250/343
4,829,448 A * 5/1989 Balding ................ A61M 5/365
                                                    128/DIG. 13
(Continued)

FOREIGN PATENT DOCUMENTS

CN        2562181 Y     7/2003
CN        2667815 Y    12/2004
(Continued)

OTHER PUBLICATIONS

International Search Report (English translation) and Written Opinion of International Application No. PCT/CN2016/079252, dated Jun. 1, 2016, 8 pages.
(Continued)

*Primary Examiner* — Gims S Philippe
(74) *Attorney, Agent, or Firm* — Westman, Champlin & Koehler, P.A.

(57) ABSTRACT

A display device includes a detecting drive unit, an air cleanliness detecting unit and an air cleanliness indicating unit. The air cleanliness detecting unit is configured to detect air cleanliness under the driven of the detecting drive unit and to transmit a detecting result to the air cleanliness indicating unit. The air cleanliness indicating unit is configured to indicate the air cleanliness based on the detecting result of the air cleanliness detecting unit. The display device of the disclosure can conveniently detect the air cleanliness so that a user can live more healthily.

16 Claims, 4 Drawing Sheets

(51) Int. Cl.
*H04M 1/725* (2006.01)
*B01D 50/00* (2006.01)
*G01N 15/14* (2006.01)
*G06K 9/00* (2006.01)
*H04N 5/232* (2006.01)
*G08B 21/12* (2006.01)

(52) U.S. Cl.
CPC ..... *G06K 9/00624* (2013.01); *G06K 9/00785* (2013.01); *G08B 21/12* (2013.01); *H04M 1/725* (2013.01); *H04N 5/23267* (2013.01); *H04M 1/72522* (2013.01); *H04M 2250/12* (2013.01)

(58) Field of Classification Search
USPC ......... 348/122, 744; 700/275; 345/204, 633; 250/34
See application file for complete search history.

(56) References Cited

U.S. PATENT DOCUMENTS

| | | | |
|---|---|---|---|
| 2008/0045156 A1 | 2/2008 | Sakhpara | |
| 2008/0092742 A1 | 4/2008 | Marra | |
| 2011/0279788 A1* | 11/2011 | Nakajima | B01D 46/008 353/61 |
| 2012/0151885 A1* | 6/2012 | Nishihata | B01D 46/0065 55/289 |
| 2012/0154348 A1* | 6/2012 | Okuno | C12Q 1/06 345/204 |
| 2012/0154694 A1* | 6/2012 | Nishihata | G03B 21/16 348/744 |
| 2013/0211599 A1* | 8/2013 | Yachiku | G05B 19/02 700/275 |
| 2014/0232747 A1* | 8/2014 | Sugimoto | G06F 3/011 345/633 |
| 2017/0193788 A1* | 7/2017 | Kim | G08B 21/12 |

FOREIGN PATENT DOCUMENTS

| | | |
|---|---|---|
| CN | 101603912 A | 12/2009 |
| CN | 201733362 U | 2/2011 |
| CN | 103263827 A | 8/2013 |
| CN | 103412086 A | 11/2013 |
| CN | 104214872 A | 12/2014 |
| CN | 203981542 U | 12/2014 |
| CN | 104394251 A | 3/2015 |
| CN | 104857798 A | 8/2015 |
| DE | 20 2007 018 768 U1 | 5/2009 |
| KR | 2003-0097437 A | 12/2003 |

OTHER PUBLICATIONS

English translation of Box No. V of the Written Opinion for the International Searching Authority for International Application No. PCT/CN2016/079252, 2 pages.
Rejection Decision for Chinese Patent Application No. 201510227976.7, dated Mar. 1, 2017, 12 pages.
Third Office Action, including Search Report, for Chinese Patent Application No. 201510227976.7, dated Nov. 21, 2016, 14 pages.
Second Office Action for Chinese Patent Application No. 201510227976.7, dated Jul. 8, 2016, 6 pages.
First Office Action, including Search Report, for Chinese Patent Application No. 201510227976.7, dated Mar. 1, 2016, 11 pages.

* cited by examiner

DISPLAY DEVICE

CROSS-REFERENCE TO RELATED APPLICATION

This application is a Section 371 National Stage Application of International Application No. PCT/CN2016/079252, filed on Apr. 14, 2016, entitled "DISPLAY DEVICE", which claims priority to Chinese Application No. 201510227976.7, filed on May 6, 2015, incorporated herein by reference in their entirety.

BACKGROUND OF THE INVENTION

Field of the Invention

Embodiments of the present disclosure relate to a field of display technique, in particular to a display device.

Description of the Related Art

With the increasing attention to the health and gradual deterioration of the environment, the demand for healthy products is increasingly larger and higher. Especially fog and haze weather is frequently occurred, people are worried about air quality increasingly. Therefore, products such as masks, sprinklers and the like to cope with this status are increasingly developed. However, in field of display technique, there is no any display device specifically designed to cope with the poor air quality, especially to cope with fog and haze.

SUMMARY OF THE INVENTION

An object of the disclosure is to provide a display device to detect fog and haze or even remove dust.

According to one aspect of the disclosure, there is provided a display device comprising a detecting drive unit, an air cleanliness detecting unit and an air cleanliness indicating unit, wherein the air cleanliness detecting unit is configured to detect air cleanliness under the driven of the detecting drive unit and to transmit a detecting result to the air cleanliness indicating unit, and the air cleanliness indicating unit is configured to indicate the air cleanliness based on the detecting result of the air cleanliness detecting unit.

Alternatively, the air cleanliness detecting unit comprises an air particulate detecting module and an air cleanliness determining module, wherein the air particulate detecting module is configured to detect a content of particulate in the air under the driven of the detecting drive unit and to transmit a detecting result to the air cleanliness determining module, and the air cleanliness determining module is configured to determine the air cleanliness to which the detecting result of the air particulate detecting module corresponds based on a correspondence between the content of the particulate and the air cleanliness stored therein and to transmit the corresponding air cleanliness to the air cleanliness indicating unit to indicate the corresponding air cleanliness by the air cleanliness indicating unit.

Alternatively, the display device further comprises an image display unit and an image display drive unit for driving the image display unit to display an image, wherein the air cleanliness indicating unit is integrated into the image display unit.

Alternatively, the display device further comprises an image display unit, a housing enclosing the image display unit and an image display drive unit for driving the image display unit to display an image, wherein the air cleanliness indicating unit is disposed on the housing.

Further alternatively, the air cleanliness indicating unit comprises an indicating lamp capable of displaying different colors to indicate the air cleanliness through the color displayed by the indicating lamp, or the air cleanliness indicating unit comprises a digital display screen to indicate the air cleanliness through a digital displayed on the digital display screen.

Alternatively, the air cleanliness indicating unit comprises a voice indicating unit for indicating the air cleanliness determined by the air cleanliness determining module by means of voice broadcast.

Further alternatively, the air cleanliness detecting unit further comprises an air cleanliness level indicating voice storing module in which a mapping relationship table of the air cleanliness and an air cleanliness level is stored to indicate the air cleanliness level by the voice indicating unit based on the air cleanliness determined by the air cleanliness determining module.

Alternatively, the display device further comprises a switch module for controlling the detecting drive unit to be activated or shut-off.

Further alternatively, the display device further comprises a dust removal unit for cleaning air around the display device under control of the detecting result of the air cleanliness detecting unit.

Further alternatively, the dust removal unit comprises a dust removal drive module and a dust removal cleaning module, the dust removal drive module is configured to be activated or shut-off under the control of the detecting result of the air cleanliness detecting unit, and the dust removal cleaning module is configured to clean the air around the display device under the driven of the dust removal drive module.

Further alternatively, the dust removal unit further comprises a dust removal switch module for selectively activating or shutting off the dust removal drive module.

Further alternatively, the dust removal module comprises at least one of a spay dust remover, an air dust remover, an ultrasonic transmitting dust remover and an electrostatic dust remover Further alternatively, the display device further comprises an image display unit, a housing enclosing the image display unit and an image display drive unit for driving the image display unit to display an image, wherein the housing is provided with a dust removal result display unit for displaying a dust removal result of the dust removal unit.

Alternatively, the display device further comprises an image display unit and an image display drive unit for driving the image display unit to display an image, wherein a dust removal result of the dust removal unit is displayed through the image display unit.

Further alternatively, the dust removal unit comprises a dust removal agent storing module into which a chemical agent for removing dust is stored to clean the air around the display device through the chemical agent stored therein.

The display device according to the embodiments of the disclosure provides the following advantageous effects.

Compared with the existing display device, the display device according to the embodiments is additionally provided with functions of detecting and indicating the air cleanliness. In particular, the air cleanliness detecting unit can detect an air quality of an environment in which a user utilizing the display device is locating and then the air cleanliness indicating unit indicates the air quality of the environment to the user, so that the user can take certain corresponding actions based on the current air quality. In a case where the display device further comprises the dust removal unit, it is possible to improve the air quality of the environment in which the user is locating so that the living of the user is healthier.

DETAILED DESCRIPTION OF PREFERRED EMBODIMENTS OF THE INVENTION

Embodiments of the disclosure will be described in detail below with reference to the accompanying drawings so that those skilled in the art can fully understand the technical solution thereof.

Figure 1:
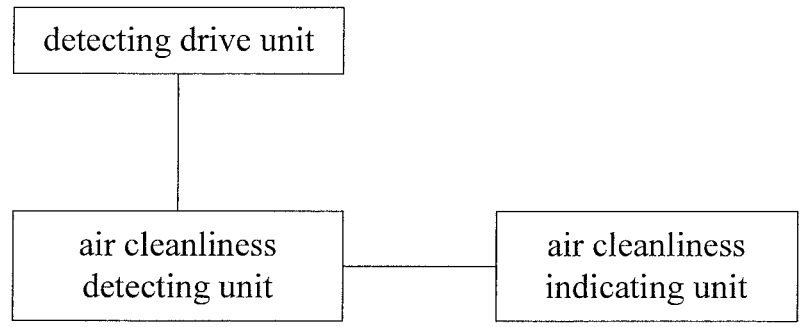
FIG. 1 is a schematic view of a display device according to an exemplary embodiment of the disclosure.

According to an exemplary embodiment of the disclosure, there is provided a display device comprising a detecting drive unit, an air cleanliness detecting unit and an air cleanliness indicating unit, as shown in FIG. 1. The air cleanliness detecting unit is configured to detect air cleanliness under the driven of the detecting drive unit and to transmit a detecting result to the air cleanliness indicating unit. The air cleanliness indicating unit is configured to indicate the air cleanliness based on the detecting result of the air cleanliness detecting unit.

Compared with the existing display device, the display device according to embodiment of the disclosure is additionally provided with functions of detecting and indicating the air cleanliness. In particular, the air cleanliness detecting unit can detect an air quality of an environment in which an user utilizing the display device is locating and then the air cleanliness indicating unit indicates the air quality of the environment to the user, so that the user can take certain corresponding actions based on the current air quality to realize more healthy living.

Figure 2:
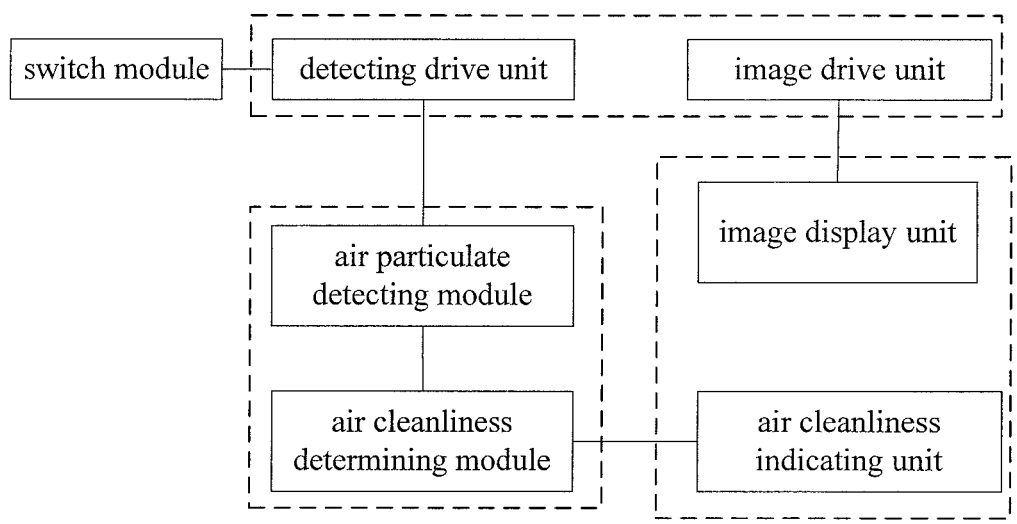
FIG. 2 is a schematic view of a particular structure of a display device according to an exemplary embodiment of the disclosure.

As shown in FIG. 2, the air cleanliness detecting unit of the display device according to embodiments of the disclosure may comprise an air particulate detecting module such as an air particulate detecting sensor and an air cleanliness determining module. The air particulate detecting module is configured to be activated under the driven of the detecting drive unit to detect a content of particulate in the air and to transmit the detecting result to the air cleanliness determining module. The air cleanliness determining module is configured to determine the air cleanliness to which the detecting result of the air particulate detecting module corresponds based on a correspondence between the content of the particulate and the air cleanliness stored therein and transmit the corresponding air cleanliness (the detecting result of the air cleanliness detecting unit) to the air cleanliness indicating unit so as to indicate the corresponding air cleanliness by the air cleanliness indicating unit. In some embodiments of the disclosure, the air cleanliness detecting unit may be disposed on an edge or a rear face of a housing of the display device.

As illustrated in FIG. 2, the above display device may further comprise a switch module for controlling the detecting drive unit to be activated or shut-off. Since the display device has the switch module, it is possible to selectively switch on or switch off the detecting drive unit. When the air cleanliness of an ambient air is visually substantially good, it is not necessary to activate the detecting drive unit, thereby saving electrical power of the display device.

In addition, as shown in FIG. 2, the above display device may further comprise an image display unit and an image display drive unit (i.e., an image drive unit in drawings). The image display drive unit is configured to drive the image display unit to display an image. The air cleanliness indicating unit may be integrated into the image display unit. The display device will be described below taking a mobile phone as an example. Of course, the display device according to embodiments of the disclosure is not limited to the mobile phone, and may include a tablet, a television and other display devices. The image display unit is a display screen of the mobile phone. In this case, the air cleanliness indicating unit may be integrated into the image display unit. In other words, the display screen of the mobile phone may display the air cleanliness. Particularly, information indicated by the air cleanliness indicating unit may be displayed on an edge of the display screen similar to signal identification and power identification of the mobile phone. At the same time, such displayed information will not affect a normal display of other contents on the display screen. Of course, the information indicated by the air cleanliness indicating unit may be displayed in the middle of the display screen of the mobile phone.

Figure 3:
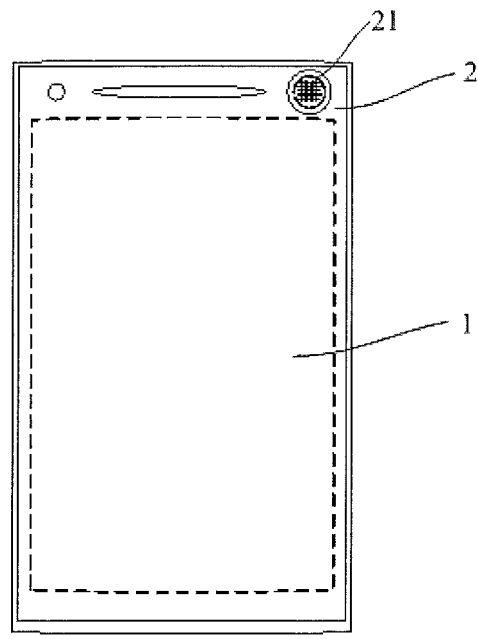
FIG. 3 is a schematic structural view of a mobile phone as a display device according to an exemplary embodiment of the disclosure.

Alternatively, as shown in FIG. 3, in addition to the image display unit 1, the display device further comprises a housing 2 enclosing the image display unit 1. In this case, the air cleanliness indicating unit may be disposed on the housing 2.

Similarly, the display device will be described below taking the mobile phone as an example. The air cleanliness indicating unit is an indicating lamp 21 capable of displaying different colors. The indicating lamp 21 is disposed on the housing 2 to indicate the air cleanliness through a color displayed by the indicating lamp 21. Alternatively, the air cleanliness indicating unit may be a digital display screen disposed on the housing 2 to indicate the air cleanliness through a digital displayed on the digital display screen. Of course, the air cleanliness indicating unit may also be an indicating lamp 21 displaying one color only. The air cleanliness may be indicated through brightness of the color displayed by the indicating lamp 21.

Particularly, taking the air cleanliness indicating unit being the indicating lamp 21 capable of displaying different colors as an example, as shown in FIG. 3, the indicating lamp 21 is disposed at an upper and right corner of the housing 2 of the mobile phone. When the air cleanliness does not exceed a predetermined threshold of an air quality, the indicating lamp 21 may display the blue color, and when the air cleanliness exceeds the predetermined threshold of the air quality, for example reaches a severe fog and haze value, the indicating lamp 21 may display the red color while flashing.

Figure 5:
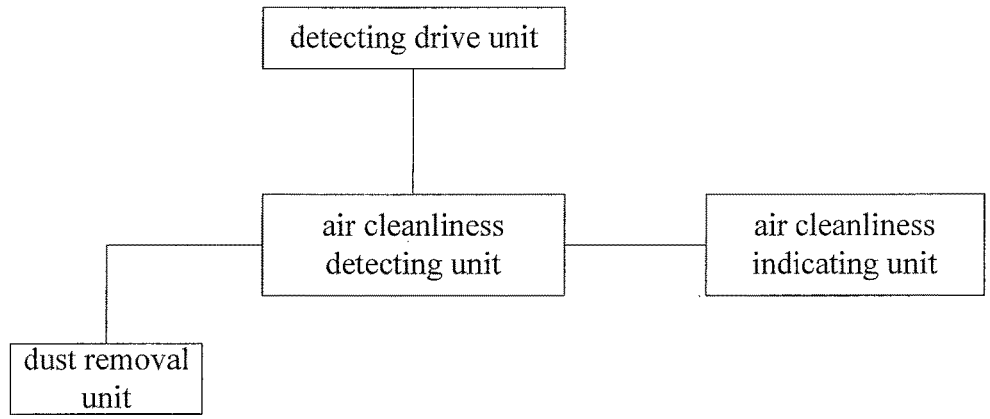
FIG. 5 is a schematic view of a display device including a dust removal unit according to an exemplary embodiment of the disclosure.

In some embodiments of the disclosure, the display device not only has the function of detecting the air cleanliness but also has a function of cleaning the air. For example, as shown in FIG. 5, the display device further comprises a dust removal unit for cleaning the air around the display device under the control of the detecting result of the air cleanliness detecting unit.

In other words, when the detecting result of the air cleanliness detecting unit shows that the cleanliness of the current air is in a polluted state, the dust removal unit is activated to clean the air around the display device so that the user is located in a cleaning and healthy environment when utilizing the display device.

Particularly, the above dust removal unit may comprise a dust removal drive module and a dust removal cleaning module. The dust removal drive module is configured to be activated or shut off under the control of the detecting result of the air cleanliness detecting unit. The dust removal cleaning module is configured to clean the air around the display device under the driven of the dust removal drive module.

Further, the above dust removal unit may further comprise a dust removal switch module for selectively switching on or switching off the dust removal drive module. Of course, the dust removal unit according to the embodiment may not be provided with the dust removal switch module. In this case, when the air cleanliness detecting unit detects that the environment in which the display device is located is polluted, the dust removal unit can be automatically activated based on this detecting result to automatically clean the air around the display device. In some embodiments of the disclosure, the dust removal unit may be disposed on the edge or the rear face of the housing of the display device.

The dust removal cleaning module may comprise at least one of a spay dust remover, an air dust remover, an ultrasonic transmitting dust remover and an electrostatic dust remover.

Figure 6:
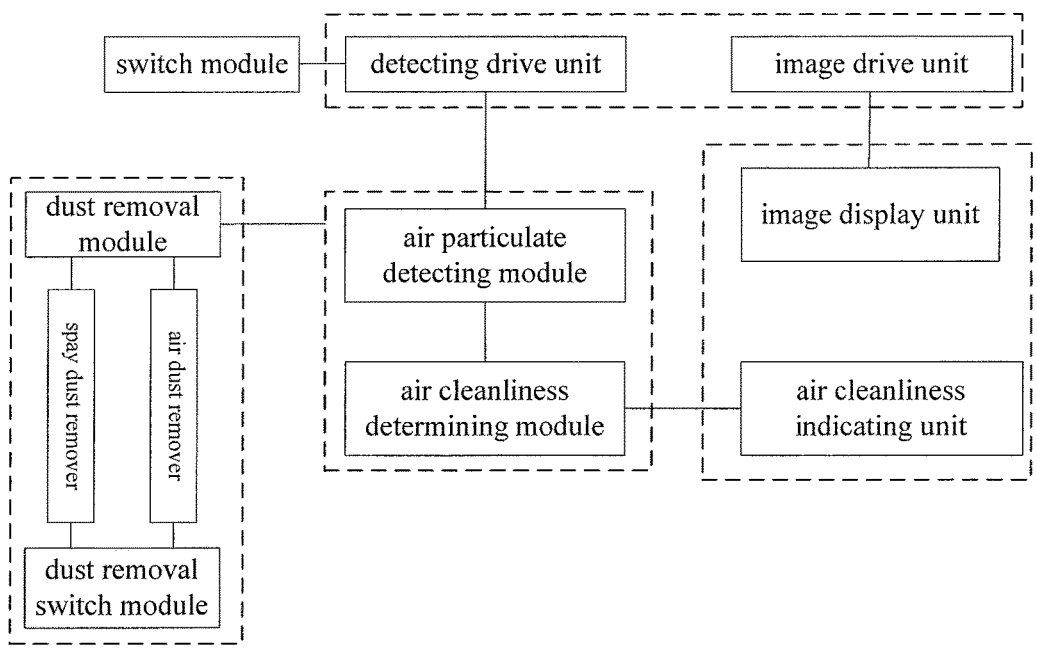
FIG. 6 is a schematic view of a particular structure of a display device including a dust removal unit according to an exemplary embodiment of the disclosure.

As shown in FIG. 6, the dust removal cleaning module includes the spay dust remover and the air dust remover. A dust discharging outlet of each of the spay dust remover and the air dust remover has a grid structure. The dust removal switch module may selectively activate at least one of the spay dust remover and the air dust remover as desired to clean the air around the display device, i.e., performing a dust removal process on the environment in which the display device is located. A dust removal result of the dust removal cleaning module may be displayed through a dust removal result display unit such as a digital display screen or other display elements disposed on the housing of the display device. Alternatively, the dust removal result of the dust removal cleaning module may also be displayed through the image display unit of the display device.

Figure 7:
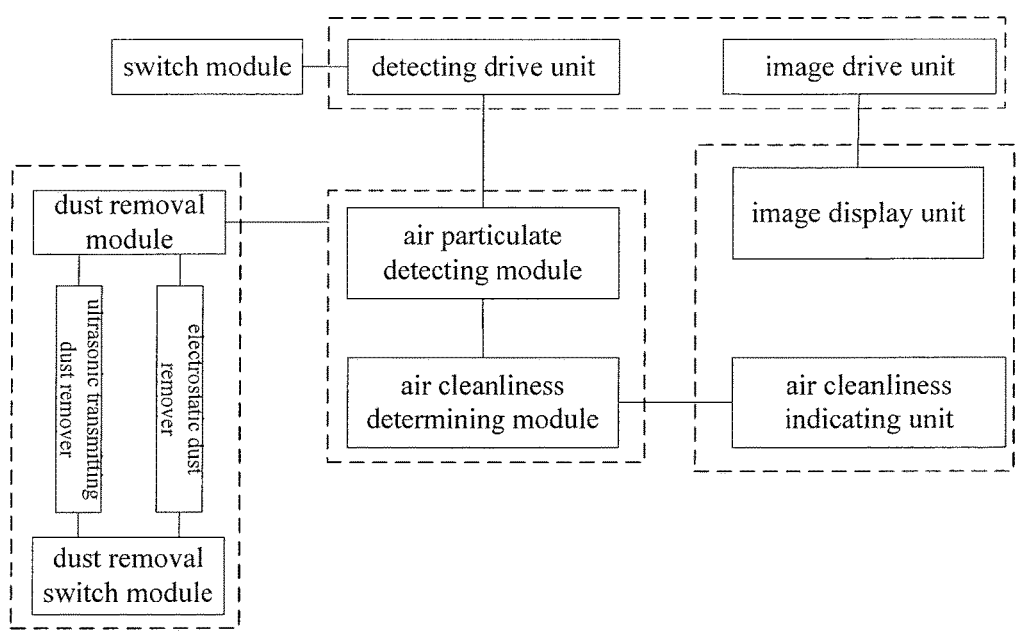
FIG. 7 is a schematic view of another particular structure of a display device including a dust removal unit according to an exemplary embodiment of the disclosure

As illustrated in FIG. 7, the dust removal cleaning module may include the ultrasonic transmitting dust remover and the electrostatic dust remover. The dust removal switch module may selectively activate at least one of the ultrasonic transmitting dust remover and the electrostatic dust remover. Particularly, it is possible to clean the particulates in the air around the display device through transmitting an ultrasonic by the ultrasonic transmitting dust remover and/or releasing electrostatic charges by the electrostatic dust remover, thereby cleaning the air around the display device.

Note that, frequency and type of the ultrasonic transmitting dust remover and type and charge size, charge releasing structure and the like of the electrostatic dust remover are not limited in the embodiments of the disclosure, and may employ the existing any other types structures and designs having dust removal and fog and haze reducing functions. Likewise, the dust removal result of the dust removal cleaning module may be displayed through the dust removal result display unit such as a digital display screen or other display elements disposed on the housing of the display device. Alternatively, the dust removal result of the dust removal cleaning module may also be displayed through the image display unit of the display device.

Alternatively, the dust removal unit of the display device may also comprise a dust removal agent storing module for storing a chemical agent for specially removing the dust. The chemical agent may be various types of the existing chemical agents having the dust removal function and the embodiments of the disclosure are not limited thereto. Therefore, in the embodiment, it is also possible to clean the air around the display device by means of the chemical agent stored in the dust removal agent storing module.

Figure 4:
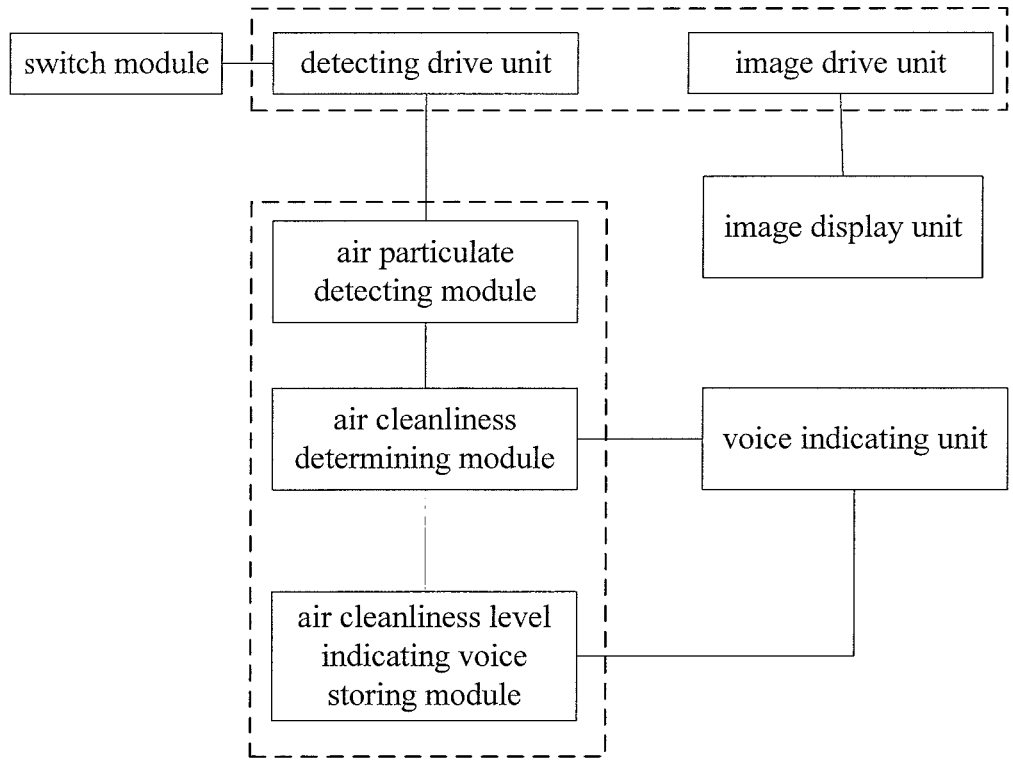
FIG. 4 is a schematic view of a display device according to another exemplary embodiment of the disclosure.

In some embodiments of the disclosure, the air cleanliness indicating unit may be a voice indicating unit for indicating the air cleanliness (i.e., the air cleanliness corresponding to the detecting result of the air particulate detecting module) determined by the air cleanliness determining module by means of voice broadcast, as shown in FIG. 4.

In other words, the air cleanliness indicating unit informs the user utilizing the display device of the detecting result of the air cleanliness detecting unit of the display device by means of the voice broadcast form.

The air cleanliness detecting unit may further comprise an air cleanliness level indicating voice storing module in which a mapping relationship table of the air cleanliness and an air cleanliness level is stored so as to indicate the user of the air cleanliness level by the voice indicating unit based on the air cleanliness determined by the air cleanliness determining module.

Particularly, as shown in FIG. 4, firstly, under the control of the switch module, the detecting drive unit is activated to drive the air particulate detecting module to detect the content of the particulates in the air around the display device. Next, the air cleanliness determining module determines the air cleanliness corresponding to the detecting result of the air particulate detecting module based on the detecting result and transmits the determining result to the air cleanliness level indicating voice storing module and the voice indicating unit so as to voice broadcast the air cleanliness level and indicate the current air quality to the user. Note that, the information broadcasted by the voice indicating unit may be different music, different tunes of one music, individuated voice such as anti fog and haze tips for warning the use of wearing a mask or suggesting the user not going out as far as possible or the like.

It should be understood that the above embodiments are merely the exemplary implementations for illustrating the principle of the disclosure. The disclosure, however, is not limited thereto. It is possible for those skilled in the art to make various changes or modifications without departing from the spirit and scope of the disclosure, and these changes or modifications should fall within the scope of the disclosure.

What is claimed is:

1. A display device comprising a detecting drive unit, an air cleanliness detecting unit, an air cleanliness indicating unit and a dust removal unit, wherein, the display device comprises a housing;

the air cleanliness detecting unit is disposed on an edge or a rear face of the housing of the display device and configured to detect air cleanliness under the driven of the detecting drive unit and to transmit a detecting result to the air cleanliness indicating unit; and the air cleanliness indicating unit is configured to indicate an air cleanliness based on the detecting result of the air cleanliness detecting unit; and the dust removal unit is disposed on the edge or the rear face of the housing of the display device and configured to clean air around the display device under the control of the detecting result of the air cleanliness detecting unit; and the dust removal unit comprises a dust removal drive module and a dust removal cleaning module, the dust removal drive module configured to be activated or shut-off under the control of the detecting result of the air cleanliness detecting unit, and the dust removal cleaning module configured to clean the air around the display device under the driven of the dust removal drive module.

2. The display device according to claim 1, wherein, the air cleanliness detecting unit comprises an air particulate detecting module and an air cleanliness determining module;

the air particulate detecting module is configured to detect a content of particulate in the air under the driven of the detecting drive unit and to transmit a detecting result to the air cleanliness determining module; and the air cleanliness determining module is configured to determine the air cleanliness to which the detecting result of the air particulate detecting module corresponds based on a correspondence between the content of the particulate and the air cleanliness stored therein and to transmit the corresponding air cleanliness to the air cleanliness indicating unit so as to indicate the corresponding air cleanliness by the air cleanliness indicating unit.

3. The display device according to claim 1, further comprising an image display unit and an image display drive unit for driving the image display unit to display an image, wherein the air cleanliness indicating unit is integrated into the image display unit.

4. The display device according to claim 1, further comprising an image display unit, and an image display drive unit for driving the image display unit to display an image, wherein the housing encloses the image display unitm and the air cleanliness indicating unit is disposed on the housing.

5. The display device according to claim 4, wherein the air cleanliness indicating unit comprises an indicating lamp capable of displaying different colors to indicate the air cleanliness through the color displayed by the indicating lamp; or wherein the air cleanliness indicating unit comprises a digital display screen to indicate the air cleanliness through a digital displayed on the digital display screen.

6. The display device according to claim 2, wherein the air cleanliness indicating unit comprises a voice indicating unit for indicating the air cleanliness determined by the air cleanliness determining module by means of voice broadcast.

7. The display device according to claim 6, wherein the air cleanliness detecting unit further comprises an air cleanliness level indicating voice storing module in which a mapping relationship table of the air cleanliness and an air cleanliness level is stored to indicate the air cleanliness level by the voice indicating unit based on the air cleanliness determined by the air cleanliness determining module.

8. The display device according to claim 1, further comprising a switch module for controlling the detecting drive unit to be activated or shut-off.

9. The display device according to claim 1, wherein the dust removal unit further comprises a dust removal switch module for selectively activating or shutting off the dust removal drive module.

10. The display device according to claim 1, wherein the dust removal cleaning module comprises at least one of a spay dust remover, an air dust remover, an ultrasonic transmitting dust remover and an electrostatic dust remover.

11. The display device according to claim 1, further comprising an image display unit, and an image display drive unit for driving the image display unit to display an image, wherein the housing encloses the image display unit, and the housing is provided with a dust removal result display unit for displaying a dust removal result of the dust removal unit.

12. The display device according to claim 1, further comprising an image display unit and an image display drive unit for driving the image display unit to display an image, wherein a dust removal result of the dust removal unit is displayed through the image display unit.

13. The display device according to claim 1, wherein the dust removal unit comprises a dust removal agent storing module into which a chemical agent for removing dust is stored to clean the air around the display device by means of the chemical agent stored therein.

14. The display device according to claim 2, further comprising an image display unit and an image display drive unit for driving the image display unit to display an image, wherein the air cleanliness indicating unit is integrated into the image display unit.

15. The display device according to claim 2, further comprising an image display unit, and an image display drive unit for driving the image display unit to display an image, wherein the housing unit encloses teh image display unit, and the air cleanliness indicating unit is disposed on the housing.

16. The display device according to claim 2, further comprising a switch module for controlling the detecting drive unit to be activated or shut-off.

* * * * *